US011452789B2

(12) United States Patent
Moser et al.

(10) Patent No.: US 11,452,789 B2
(45) Date of Patent: Sep. 27, 2022

(54) DEVICE FOR ISOLATION, CLEANING, DRYING, DECONTAMINATION AND SANITIZATION OF CONTAMINATED COMPONENTS

(71) Applicant: Amsonic AG, Biel/Bienne (CH)

(72) Inventors: Hansruedi Moser, Magglingen/Macolin (CH); Jörg Dolmetsch, Grenchen (CH)

(73) Assignee: AMSONIC AG, Biel/Bienne (CH)

( * ) Notice: Subject to any disclaimer, the term of this patent is extended or adjusted under 35 U.S.C. 154(b) by 0 days.

(21) Appl. No.: 17/284,141

(22) PCT Filed: Oct. 19, 2018

(86) PCT No.: PCT/EP2018/078698
§ 371 (c)(1),
(2) Date: Apr. 9, 2021

(87) PCT Pub. No.: WO2020/078562
PCT Pub. Date: Apr. 23, 2020

(65) Prior Publication Data
US 2021/0308313 A1 Oct. 7, 2021

(51) Int. Cl.
*A61L 2/00* (2006.01)
*B01J 10/00* (2006.01)
*A61L 2/26* (2006.01)
*A61L 2/20* (2006.01)
(Continued)

(52) U.S. Cl.
CPC ............... *A61L 2/26* (2013.01); *A61L 2/208* (2013.01); *B01D 46/4263* (2013.01);
(Continued)

(58) Field of Classification Search
CPC . A61L 2/00; A61L 2/0082; A61L 2/20; A61L 2/208
(Continued)

(56) References Cited

U.S. PATENT DOCUMENTS 4,459,270 A * 7/1984 Leppard ............... B01J 23/8966
423/248
6,010,400 A 1/2000 Krainiak et al.
(Continued)

FOREIGN PATENT DOCUMENTS

EP         2517734 A1    10/2012
WO   2004028573 A1     4/2004
(Continued)

OTHER PUBLICATIONS

International Search Report and Written Opinion in PCT/EP2018/078698 dated Jul. 9, 2019, 13 pages.

*Primary Examiner* — Monzer R Chorbaji
(74) *Attorney, Agent, or Firm* — Pearne & Gordon LLP

(57) ABSTRACT

The present invention relates to a device for isolating and cleaning contaminated components comprising a chamber, an entrance door through which components to be isolated and cleaned are introducible into the chamber, means configured to deliver washing solution into the chamber and onto the components to be cleaned, a drying system configured to dry the chamber as well as its content, wherein the device further comprises an exhaust filter system attached to the air exhaust of the chamber, the exhaust filter system comprising a pipe, at least one filter and a blower, the exhaust filter system being configured to be able to bring the chamber under a pressure lower than atmospheric pressure by means of the blower all the time the chamber is closed. The present invention also relates to a corresponding method for isolating and cleaning contaminated components with the aforementioned device.

20 Claims, 6 Drawing Sheets

(51) Int. Cl.
  *B01D 46/42* (2006.01)
  *B08B 3/02* (2006.01)
  *B08B 3/08* (2006.01)
  *B08B 13/00* (2006.01)
  *B08B 15/02* (2006.01)
  *B01D 46/62* (2022.01)
  *B01D 46/88* (2022.01)
  *A61L 101/02* (2006.01)

(52) U.S. Cl.
  CPC ............. *B01D 46/62* (2022.01); *B01D 46/88* (2022.01); *B08B 3/02* (2013.01); *B08B 3/08* (2013.01); *B08B 13/00* (2013.01); *B08B 15/026* (2013.01); *A61L 2101/02* (2020.08); *A61L 2202/121* (2013.01); *A61L 2202/122* (2013.01); *A61L 2202/13* (2013.01); *A61L 2202/17* (2013.01); *B01D 2279/55* (2013.01); *B08B 2203/007* (2013.01)

(58) Field of Classification Search
  USPC .......................................... 422/116, 292, 188
  See application file for complete search history.

(56) References Cited

U.S. PATENT DOCUMENTS 8,486,332 B1* 7/2013 Ricciardi .................. B08B 3/00
  422/33
2010/0189607 A1* 7/2010 Yokoi ....................... A61L 9/00
  422/116

FOREIGN PATENT DOCUMENTS

WO  2008116341 A2  10/2008
WO  2013186518 A1  12/2013

* cited by examiner

DEVICE FOR ISOLATION, CLEANING, DRYING, DECONTAMINATION AND SANITIZATION OF CONTAMINATED COMPONENTS

TECHNICAL FIELD OF THE INVENTION

The present invention relates to the technical field of handling of contaminated components, for instance contaminated pharmaceutical components, more specifically to their isolation and cleaning. More precisely, the present invention relates to a device for the isolation and cleaning of components contaminated with hazardous or non-hazardous ingredients, for instance active pharmaceutical ingredients. The present invention relates also to a device which is designed to be able to be used as a decontaminator in particular as pharmaceutical decontaminator. The present invention relates also to a corresponding method for isolating and cleaning contaminated components such as pharmaceutical components.

BACKGROUND OF THE INVENTION

Manufacturing industry, in particular the pharmaceutical industry, requires the highest level of safety when handling manufacturing raw materials especially when these are hazardous materials, in particular when handling pharmaceutical components that are polluted with or are containing pharmaceutical ingredients. The handling must guarantee that cross-contamination between manufactured goods, for instance drugs, is impossible and that the manufacturing staff is not exposed to hazardous material.

These objectives are mainly attained by guaranteeing that all components and devices used for the manufacturing of goods, especially drugs, are absolutely clean prior use and that handling of the components and raw materials itself is made in an isolated environment from which the raw materials cannot escape. This is of particular interest in pharma industry where it is of utmost importance that cross-contamination between drugs is avoided.

Of course, it is nothing new that absolute cleanliness is required in the field of drug manufacturing, but this requirement becomes nowadays increasingly important since active pharmaceutical ingredients (API) and highly active pharmaceutical ingredient (HAPI), i.e. the drug active products themselves, are becoming more and more potent. This implies that the smallest dose of residual API or HAPI can lead to adulteration or contamination of drug products. This can be dangerous not only for patients but also for the manufacturing employees. Contaminations of drug products represent also an economical risk for pharmaceutical companies as they may need to reclaim contaminated products, which engenders of course enormous costs.

In the last decades a number of prominent cases of drug cross-contamination were discovered. One example which led to an increased awareness of the potential for cross-contamination due to inadequate cleaning procedures is the recall of a drug product called cholestyramine resin in 1988. The bulk pharmaceutical chemical used to produce this product had become contaminated with low levels of intermediates and degradants from the production of agricultural pesticides. The cross-contamination in that case is believed to have been due to the reuse of recovered solvents. The recovered solvents had been contaminated because of a lack of control over the reuse of solvent drums. Drums that had been used to store recovered solvents from the pesticide production process were later used to store recovered solvents used for the resin manufacturing process. The firm did not have adequate controls over these solvent drums, did not do adequate testing of drummed solvents, and did not have validated cleaning procedures for the drums. Some shipments of this pesticide contaminated bulk pharmaceutical were supplied to a second facility at a different location for finishing. This resulted in the contamination of the bags used in that facility's fluid bed dryers with pesticide contamination. This in turn led to cross contamination of lots produced at that site, a site where no pesticides were normally produced.

In order to meet the high standards set by the pharmaceutical industry in term of cleanliness, special cleaning devices have been developed in the last decades. These special cleaning devices are designed to process critical components such as, fermentation containers, bottles, glassware, components of liquid- and powder-filling and packing-machines, mixers, tubes, cones, palettes, boxes, tabletting-tools, and other components from pharmaceutical, diagnostic and biotech industries (in the following called contaminated components). Roughly speaking these special devices look like oversized "dishwashers". However, these devices need to meet requirements much higher than normal "dishwashers". For instance, the washing chamber of these special cleaning devices must be designed that its surface does not have radii smaller than 30 mm and a surface roughness bigger than 0.8 µm in order to ensure that no residual raw materials, as for instance API, can remain in the chamber after completion of the cleaning procedure.

The currently existing cleaning devices, have difficulties when dealing with raw materials in form of powders because they can easily escape the cleaning device. This is particularly true for pharmaceutical applications when dealing with API in form of powders. Unfortunately, powder API represent a particular high risk of contamination since they can possibly escape into the atmosphere through the air exhaust of the cleaning devices during the cleaning procedure. Moreover, the current cleaning devices are only designed to be able to clean "open" pharmaceutical components, for instance open tubes, open containers, open boxes etc. The transfer of the polluted components into the cleaning device represents at present a particularly high risk of contamination, specifically in case of powder API. Therefore in many cases, it would be advantageous to keep the contaminated components closed, in order to avoid contamination, until these components are introduced into the cleaning devices and isolated from the environment, i.e. the exterior of the cleaning devices. Once isolated from the environment the components could be opened and cleaned.

Handling of pharmaceutical components in an isolated environment is normally done by means of so-called isolators. Isolators are devices that provide a physical and aerodynamic barrier between the external clean room environment and a work process. Gloves or robotic arms installed on the isolators are then used to manipulate the components inside the isolators. This ensures that the environment is maintained as contamination-free to safeguard handling staff. However, known isolators do not allow for automatic washing and drying of pharmaceutical components. Furthermore, as soon as the ingredients are introduced in the isolator, the isolator itself becomes a "contaminated part" that need to be cleaned before new components can be handled. Known isolators do not have a function of "self-cleaning".

In order to reduce the risk of contamination due to the handling of contaminated components, it was proposed to attach an isolator to a cleaning device, for instance to the entrance door of a cleaning device. This allows for reducing the risk of contamination due to transfer of the polluted components between the isolator and the cleaning device since the components can be kept closed or kept in a container upon introduction in the cleaning device. However, this solution does not solve the problem of the cleaning of the isolator itself. In such a configuration, i.e. an isolator attached to a cleaning device, the isolator must be "manually" cleaned before further polluted components can be introduced into the cleaning device. Furthermore, this configuration does not permit to diminish the risk of contamination due to compounds escaping the cleaning device itself. It is important to note, that during the cleaning process not only powder but also solid and semi-solid API can escape from existing cleaning device into the atmosphere mainly because of the high water temperature, close to 100° C., used during a cleaning process. The high water temperature is unfortunately sufficient to transform solid and semi-solid API into a volatile phase that can, with the help of the stream of water vapour, leak out of the cleaning device.

Furthermore, current cleaning devices to which an isolator have been attached do not permit besides cleaning and isolation of polluted components to decontaminate and sterilize these components as well as to decontaminate the isolator and the cleaning device. However, this would be very advantageous since the polluted components could then be safely introduced into the cleaning device, isolated from the environment, cleaned and decontaminated before exiting the device. This would guarantee highest possible safety for the manufacturing staff and reduce significantly the risk of cross-contamination.

Based on the state of the art, the invention at hand has the task of overcoming the aforementioned disadvantages and to propose a device and a method that allows for isolating, cleaning and decontaminating polluted pharmaceutical components in one device and in one combined process.

SUMMARY OF THE INVENTION

Thus, the object of the present invention is to propose a device and a method that allows for isolating, cleaning, drying, decontaminating and sanitization of polluted contaminated components in one device and in one combined process.

According to the present invention, these objects are achieved in particular through the elements of the two independent claims. Further advantageous embodiments follow moreover from the dependent claims and the description. Features disclosed herein in different embodiments can also be combined easily by a person who is skilled in the art.

In particular, in a first aspect, the objects of the present invention are achieved by a device for isolating and cleaning contaminated components comprising a chamber, an entrance door through which components to be isolated and cleaned are introducible into the chamber, means to deliver washing solution into the chamber and onto the components to be cleaned, a drying system configured to dry the chamber as well as its content, wherein the device further comprises an exhaust filter system attached to the air exhaust of the chamber, the exhaust filter system comprising a pipe, at least one filter and a blower, the exhaust filter system being configured to be able to bring the chamber under a pressure lower than atmospheric pressure by means of the blower all the time the chamber is closed.

Thanks to the device according to the present invention it possible to isolate and clean contaminated components while ensuring that no pollutant, in particular API, can escape the chamber of the device without being captured by the filter system. Due to the negative pressure maintained in the chamber by the blower of the exhaust filter system, the API are forced through the exhaust air filter system and in particular through the filter of this system and therefore cannot escape into the atmosphere avoiding cross-contamination or exposure of manufacturing staff to hazardous material.

In a preferred embodiment of the present invention, the exhaust filter system is configured such that air exiting the filter system has an occupational exposure limit smaller than 1 µg/m$^3$.

Since the exhaust filter system is configured such that air exiting the filter system has occupational exposure limit smaller than 1 µg/m$^3$, the device can be used in manufacturing environment where the smallest API concentration possible is required.

In a further preferred embodiment of the present invention, the exhaust filter system comprises at least one cooler. The presence of the cooler ensures that the vapour exiting the chamber of the device can be cooled down to a temperature suitable for common filter types, i.e. advantageously under 60° C., preferably under 40° C. Furthermore, the cooler allows for helping, during and after washing of the components, to condensate a part of the vapour exiting the chamber through its air exhaust. A part of the API contained in the vapour can therefore be collected in form of condensate. This allows for prolonging the lifetime of the filter of the exhaust filter system since its exposure to pollutant is reduced.

In another preferred embodiment, the exhaust filter system of the device comprises means for collecting liquid, especially for collecting condensed vapour and for guiding the collected liquid to drain means. Thus vapour that condensed both on the walls of the pipe or on the surface of the cooler can be collected by the collecting means and directed to drain means for safe disposal. Advantageously, the collected liquid is directed to the drain means of the chamber.

In a further preferred embodiment, the at least one filter of the exhaust filter system is of type HEPA. Thanks to this type of filter high filter efficiency can be attained with a small filter volume.

In a preferred embodiment of the present invention, the exhaust filter system comprises a primary and a secondary filter that are combined in a push-push filter mechanism. Thus, it is guaranteed that even if the primary filter is malfunctioning, the secondary filter, the so-called police filter, filters the air enough that air exiting the filter does not represent a danger of cross-contamination or a danger for the manufacturing staff.

In another preferred embodiment of the present invention, the push-push filter mechanism is of type bag-out. With a bag-out push-push filter mechanism, it is possible to exchange a polluted filter with a new filter while ensuring that no pollutant can escape into atmosphere during the exchange procedure.

In a further preferred embodiment of the present invention, the blower is configured to maintain a pressure in the chamber 10 Pa to 100 Pa, advantageously 30 Pa to 70 Pa and even more advantageously 40 Pa to 60 Pa, lower than atmospheric pressure all the time the chamber is closed. These pressure ranges allows for extracting all dangerous ingredient out of the chamber while requiring only a typical blower and without producing excessive energy consumption by the latter.

In another preferred embodiment, the device comprises further an exit door opposite to entrance door. This "drive-through" configuration allows for placing the device at the interface between a "polluted" space and a clean space.

In another preferred embodiment, the entrance door and/or the exit door and/or the chamber comprise at least two gloves for manipulating objects inside the chamber. Thus components can be manipulated inside the chamber and better cleaning can be obtained. Furthermore, containers and closed components can be maintained closed upon introduction into the chamber of the device and then be opened and handled with the manipulation gloves. This allows for reducing the risk of cross contamination and exposure to dangerous pollutants for the manufacturing staff.

In a further preferred embodiment, the device further comprises pressurized gas pipes attached to each glove. With the pressurized gas pipes, the gloves can be blown up inside the chamber. The gloves can thus be optimally cleaned by means of the device, at the same time or after cleaning the polluted components. In a further preferred embodiment, the device further comprises means by which an antiseptic gas is introducible into the chamber. Thanks to this the polluted components cannot only be isolated and cleaned but also decontaminated and sterilized. The device can therefore not only be used as an isolator and cleaning device but also as a pharmaceutical decontaminator.

In a further preferred embodiment, the antiseptic gas is hydrogen peroxide gas. Hydrogen peroxide can advantageously be kept in its liquid form just before being introduced in its gaseous into the chamber. Furthermore, it can easily be collected and safely disposed by the means for collecting liquid since it will condensate inside the filer system.

In a second aspect, the objects of the present invention are met by a method for isolating and cleaning polluted pharmaceutical components by means of a device according to the present invention and comprising the steps of:
 a. opening the chamber of the device,
 b. introducing the components to be cleaned into the chamber,
 c. closing the chamber,
 d. washing the components to be cleaned with heated and pressurized cleaning solution until the components are cleaned,
 e. drying the cleaned components and the chamber,
 f. opening the chamber and taking out the cleaned components,
wherein all the time the chamber is closed, a pressure 10 Pa to 100 Pa lower than atmospheric pressure is maintained inside the chamber by means of the blower of the exhaust filter system of the device.

With this method it is possible to isolate and clean pharmaceutical components while ensuring that during washing and drying of the polluted components no pharmaceutical pollutant in particular API can escape the chamber of the cleaning device without being captured by the filter system. Due to the negative pressure maintained in the chamber by the blower of the exhaust filter system, the API are forced through the exhaust air filter system and in particular through the filter of this system and cannot therefore escape into the atmosphere avoiding cross-contamination or exposure of manufacturing staff to hazardous material.

In a preferred embodiment, the cleaning device comprises manipulation gloves wherein the gloves are washed during step (d) and dried during step (e).

In a further preferred embodiment, between steps (d) and (e) the components are rinsed with an aqueous rinsing solution until a predetermined total organic carbon level and/or a predetermined conductivity of the aqueous rinsing solution is reached. Thus, by measuring the total organic carbon level and/or the conductivity of the aqueous rinsing solution is ensured that the components and the chamber is sufficiently rinsed before the drying step starts.

In another further preferred embodiment, the predetermined total organic carbon level of the aqueous rinsing solution is in the range 0.05 ppbc to 2 ppmc, advantageously in the range 0.05 ppbc to 1 ppmc, even more advantageously in the range 0.05 ppbc to 0.5 ppmc.

In another further preferred embodiment, the predetermined the conductivity of the aqueous rinsing solution is in the range 0.01 µS to 100 µS, more advantageously in the range 0.01 µS to 50 µS, even more advantageously in the range 0.01 µS to 20 µS.

In another preferred embodiment, between steps (e) and (f) an antiseptic gas is introduced in the chamber. Thus, the components are not only cleaned but also sterilized.

In a further preferred embodiment, the antiseptic gas is hydrogen peroxide gas. In this manner, the cleaned components can easily be sterilized and the antiseptic gas collected by the exhaust filter system.

In another preferred embodiment, the method is automatically operated by electronic means. With the electronic means it can be guaranteed that the isolation of the components inside the chamber, the cleaning process as well as the sterilization step can be repeated in an absolute reproducible manner. That ensures that the clean components have reproducible properties after being taken out of the cleaning device.

DETAILED DESCRIPTION OF A PREFERRED EMBODIMENT OF THE INVENTION

Figure 1:
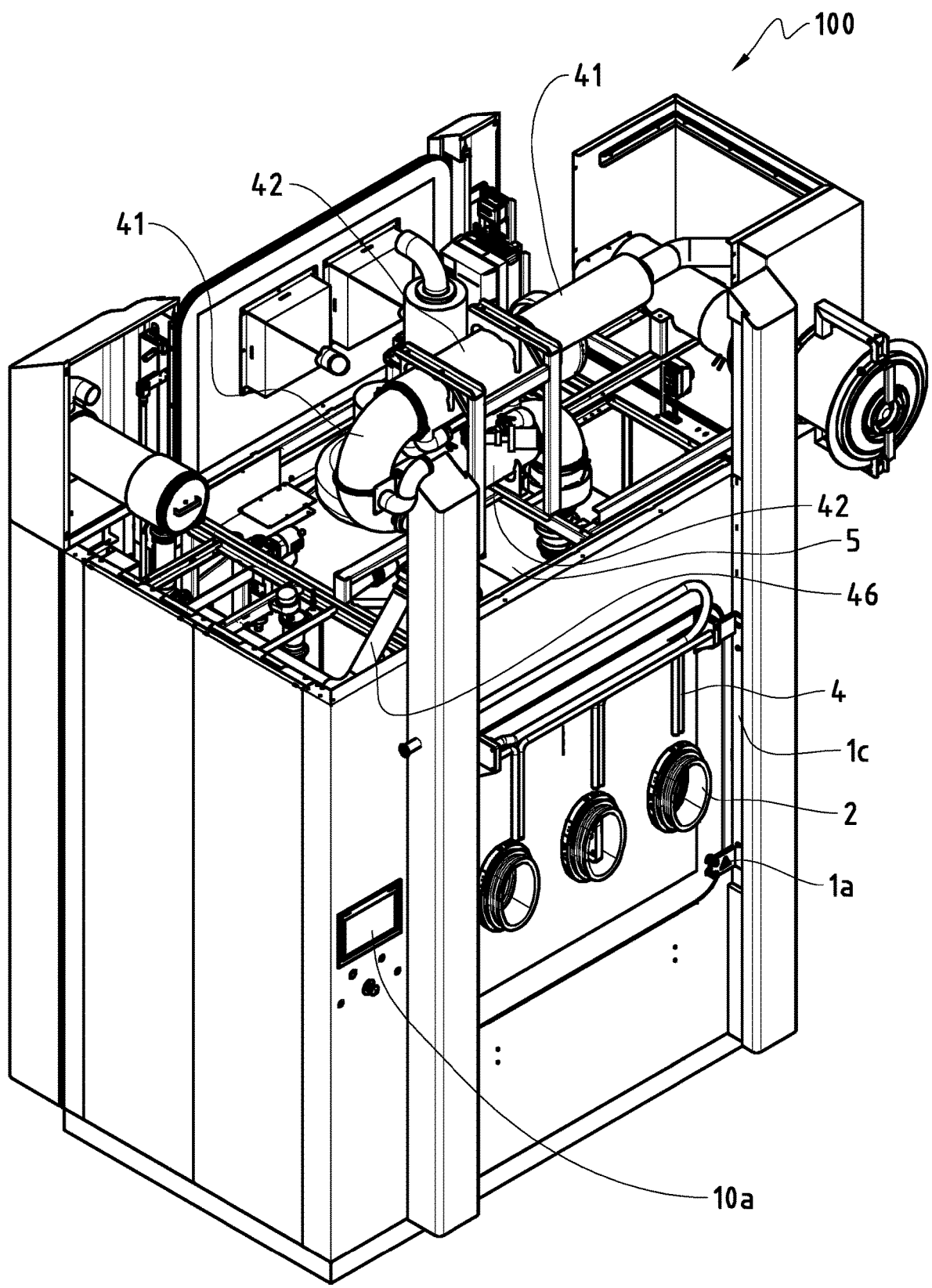
FIG. 1 shows a perspective view of a device according to a preferred embodiment of the present invention, seen from the entrance door.
Figure 2:
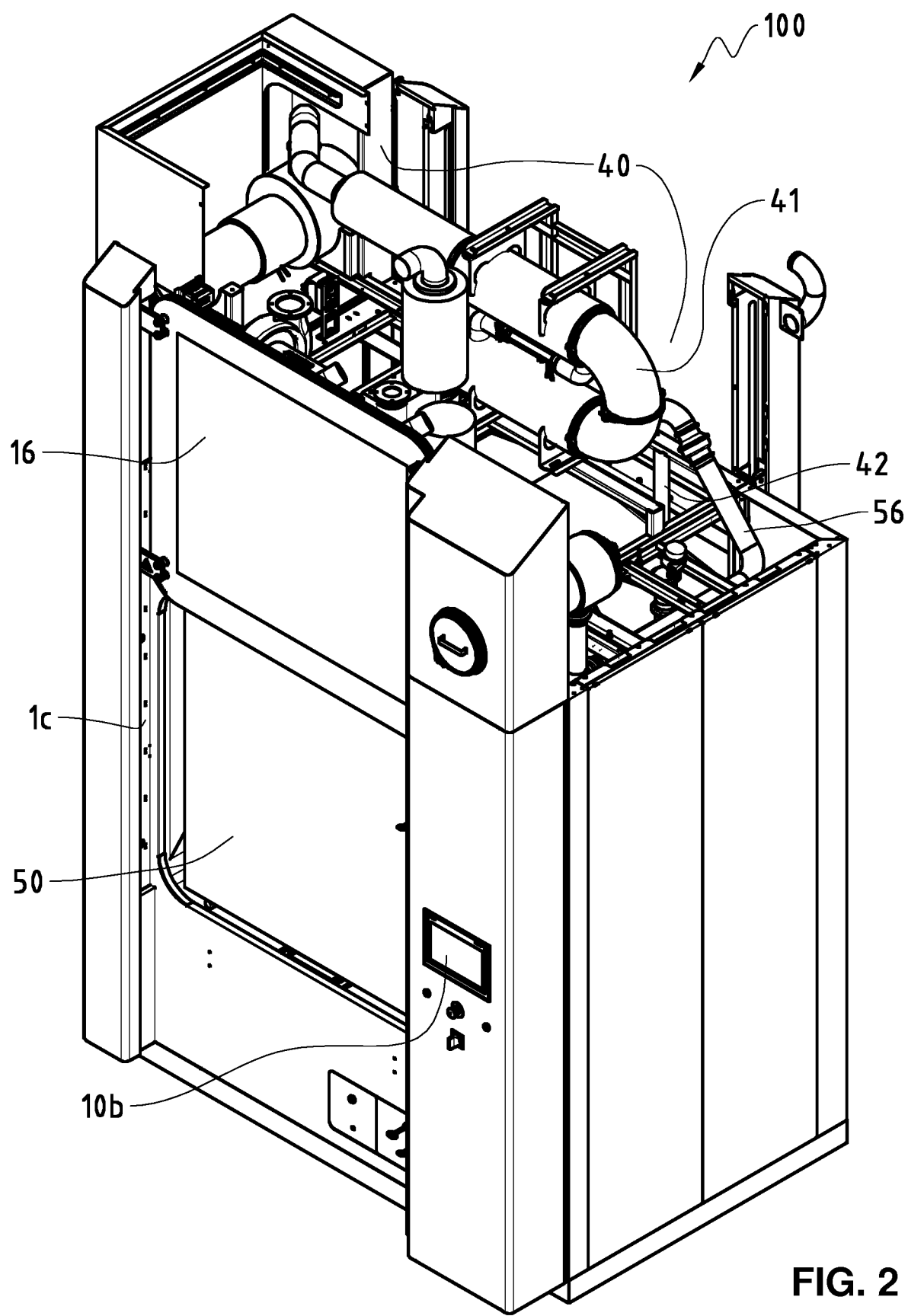
FIG. 2 shows a perspective view of a device according to a preferred embodiment of the present invention, seen from the exit door.

FIGS. 1 and 2 show perspectival views of the device 100 according to a preferred embodiment of the present invention. The device 100 comprises an entrance door 1a and an exit door 1b opposite to each other mounted on rails 1c. As illustrated in FIG. 2 the doors 1a and 1b can be slid up and down to open and close a chamber 50. The "drive-through" configuration of the device 100, i.e. the presence of two doors opposite to each other, allows for placing the device 100 at the interface between a "polluted" and a clean space of a manufacturing facility.

The doors 1a and 1b are sealable with inflatable gasket, located on the doors circumference and permit to tighten hermitically the chamber 50. Thanks to the inflatable gasket, the chamber 50 can be isolated from the rest of the room in which it is located. It can then be brought at a pressure different than atmospheric pressure, in particular at a pressure lower than atmospheric pressure (see below for more details). The device 100 can therefore be used as pharmaceutical isolator. The doors 1a and 1b are double or triple glassed to prevent heat loss and injury to the operators. The device 100 comprises doors switches by means of which it is possible to detect if the doors 1a and 1b are closed or open. The detection of the position of the doors 1a and 1b permits to ensure that the doors are in fully closed position, including pressurized and inflated door seal before polluted components can opened and a cleaning cycle can be started. Furthermore, safety inter-locks prevent that the doors can be opened before the end of a cleaning cycle. The inter-locks guarantees also that exit the door 1b cannot be opened after a not successful cleaning cycle and that both doors cannot be opened at the same time. The chamber 50 as wells as all other component of the device 100 are made of corrosion-resistant materials wherein all metal surfaces have a surface roughness Ra smaller than 0.8 µm. Drain means 60 are provided for the flow and recovery of the washing solution.

As illustrated in FIG. 1, the entrance door 1a comprises openings 2 to which manipulation gloves (not shown) are tightly attached. The manipulation gloves permits to manipulate objects inside the chamber 50. To each glove is an air pipe 4 foreseen that can be used to blow up the gloves inside the chamber 50 of the device 100. This allows for optimal cleaning of the gloves by means of the device 100. It has to be noted that instead of gloves, robot arms can be foreseen for manipulating the part inside the chamber 50. Furthermore, the gloves could also be directly attached to the chamber 50 instead to the door 1a.

As illustrated in FIGS. 1 and 2, the device 100 comprises two control boards 10a and 10b of an electronic control system 10 on the entrance and exit sides of the device 100 respectively. By means of the control system 10 and boards 10a and 10b, values measured by sensors installed on or in the device 100 can be displayed and all active elements of the device 100 such as valves, pump, blowers, heaters, coolers, dryers and doors, etc. can fully be controlled. A person skilled in the art will appreciate, by reading the description of the preferred embodiment of the present invention, that each time sensors or active elements are mentioned that either the value of the sensor can be read by means of the control 10 and displayed on the control boards 10a and 10b and/or the active elements can be controlled by these means even if not explicitly mentioned each time.

Figure 3A:
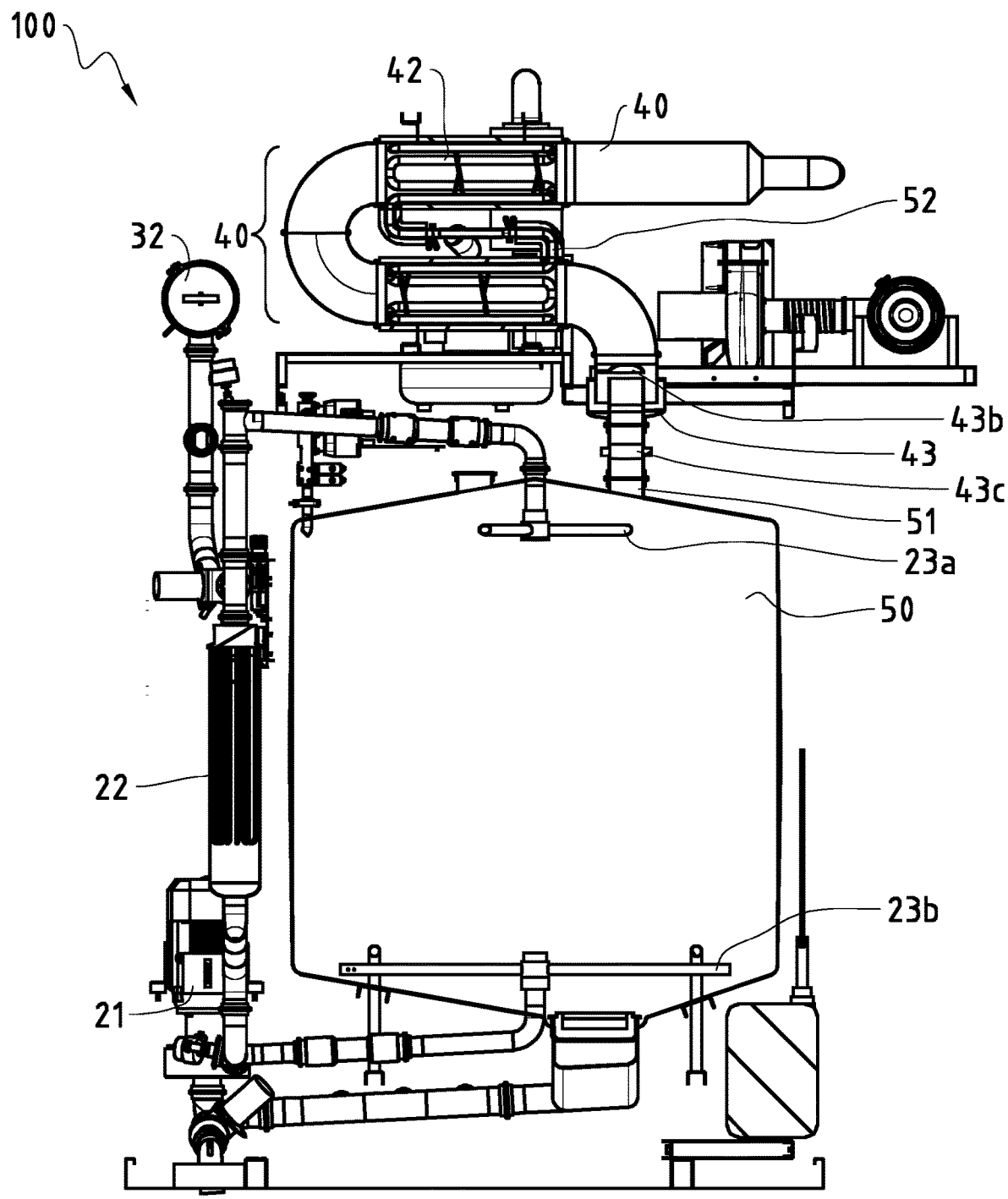
FIG. 3a shows a sectional view of a device according to a preferred embodiment of the present invention.
Figure 3B:
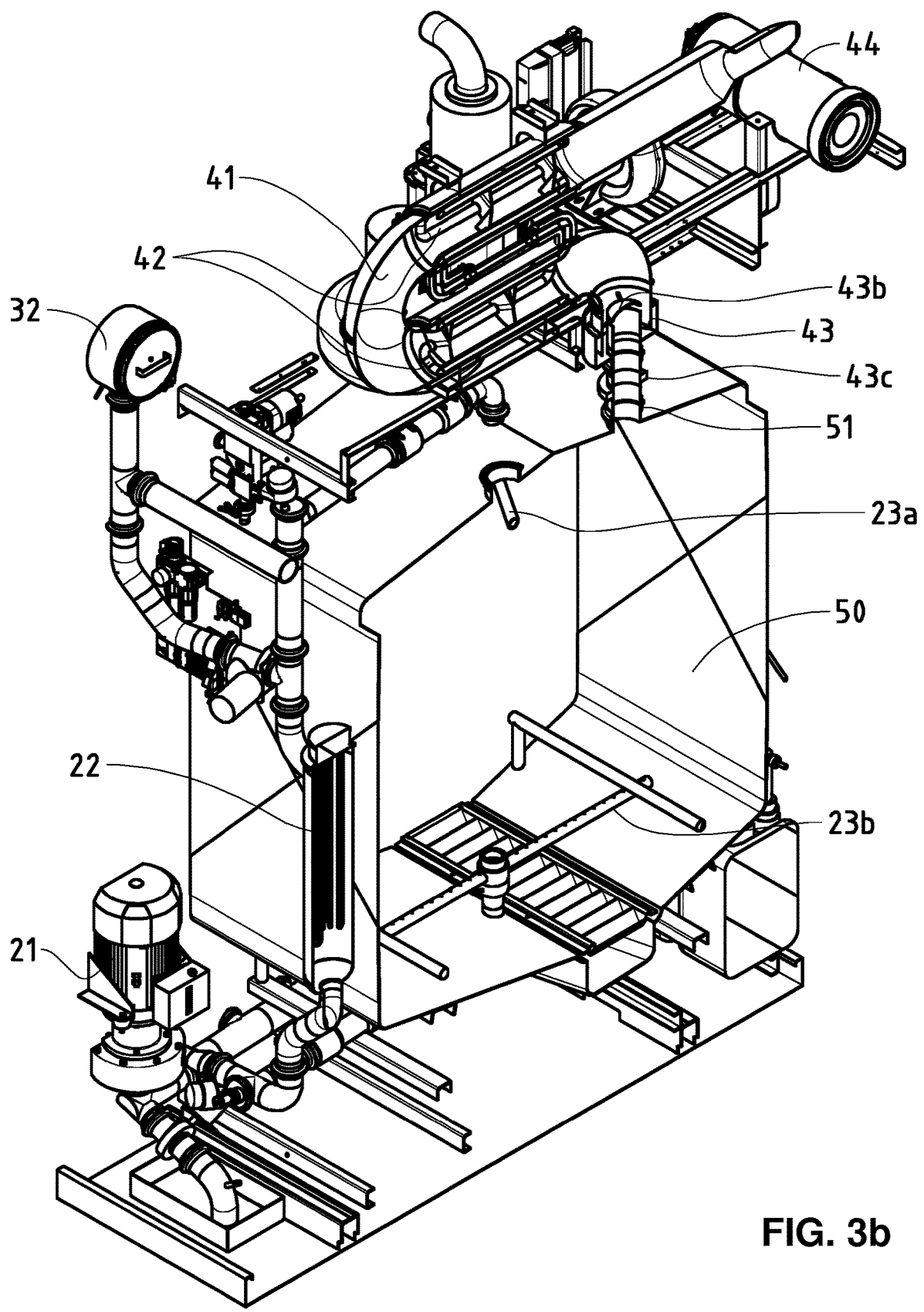
FIG. 3b shows a sectional perspective view of a device according to a preferred embodiment of the present invention.

As can be seen in FIGS. 3a and 3b which are sectional views of the device 100, the device 100 according to the preferred embodiment of the present invention comprises means 20 for exposing the components inside the chamber 50 to hot and pressurized cleaning solution. This means 20 comprises a circulation pump 21 and a heater 22 that are used to bring hot and pressurized water combined with detergent to the spray arms 23a and 23b. The concentrated detergent are kept in jerrycans 24 and mixed to hot water before the cleaning solution is delivered by the spray arms 23a and 23b. The body of pump 21 is made completely of stainless steel with a surface roughness Ra<0.8 µm in order to meet the standards of the pharmaceutical industry. As can been seen in FIG. 3, the pump 21 is preferably vertically installed for optimal drainage and is able to generate a flow of cleaning solution with a pressure of approximately 1.5 bar. A pressure sensor detects the presence of sufficient water pressure and if the pressure is too low or high an alarm is generated and stops the device. Similarly, proximity switches confirm that the spray arms 23a and 23b are rotating and generate alarms if the rotation speed is too low. The heater 22, advantageously an electric resistance heater, is designed to be able to heat the cleaning solution up to 95° C.

The device 100 comprises also an integrally heated, filtered, forced-air drying system 30 which takes advantage of the heater 22 to heat air up to 110° C. The drying system 30 is designed to force filtered heated air through every part of the circulated liquid system, i.e. to every part of the means 20 for exposing the polluted components to hot and pressurized cleaning solution. A high-pressure positive side channel blower 31 delivers the drying air heated by the heater 22 into the chamber 50 by means of the spray arms 23a and 23b. This dries the chamber and its content. In order to ensure that clean air is used by the drying system 30 the channel blower 31 is connected to a so-called high efficiency particulate air (HEPA) filter 32. A differential pressure sensor is provided to monitor the differential pressure drop across the HEPA filter 32. A further sensor is placed after the HEPA filter 32 to detect the presence of water in the air system. The system use a temperature sensor in combination with the heater 22 to adjust the air temperature. If there is insufficient airflow through the heater 22, or if the heating rate is too slow, an error message is generated onto the control boards 10a and 10b and the device 100 stops.

Figure 4:
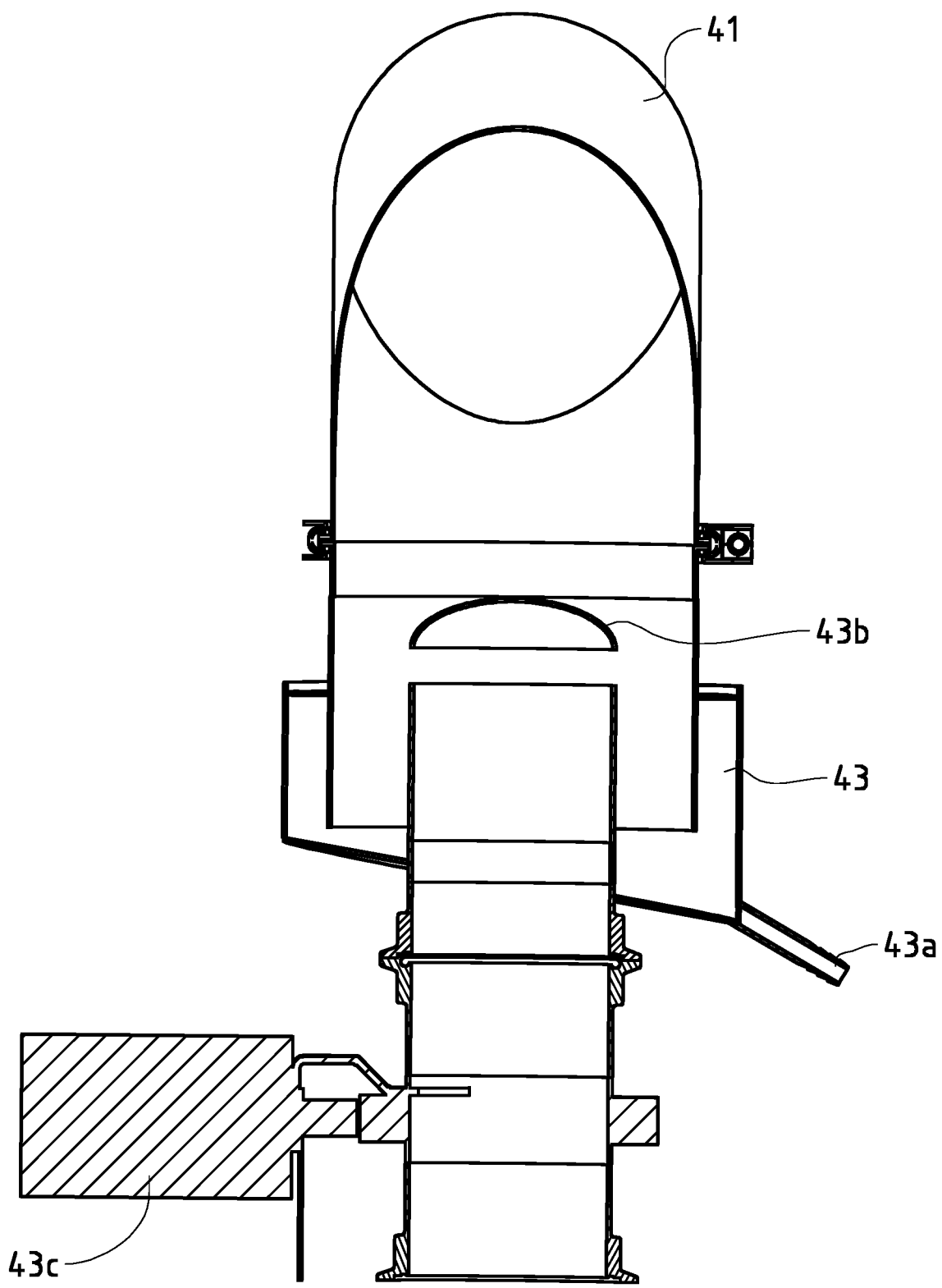
FIG. 4 shows a sectional view of the liquid collecting means of the exhaust filter system according to a preferred embodiment of the present invention.

In order to ensure, that no API can escape to the atmosphere before, the device 100 comprises an exhaust filter system 40 attached to the air exhaust 51 of the chamber 50. The exhaust filter system 40 comprises a pipe 41 with two coolers 42. By means of the coolers 42 vapour generated during the cleaning procedure and possibly containing API, can be cooled down. Part of the vapour then condensates at the pipe 41 walls or on the surface of the coolers 42. Since the pipe 41 is slightly inclined with respect to ground, condensed water vapour flows on the surface of pipe 41 in direction of a dripping pan 43 where it is collected. The dripping pan 43 comprises an exhaust pipe 43a (see FIG. 4) connected to the drain means 60 of the chamber 50. The cap 43b ensures that no liquid can flow back into the chamber 50. A valve 43c allows for isolating the pipe 41 from the chamber 50 when the doors are opened. As illustrated in FIGS. 1 and 2 the pipe 41 of the exhaust filter system is connected through the side pipe 46 to the drying system 30. This ensures that cooled air with a relative low humidity content can be added to the air flowing through the exhaust filter system. This allows for reducing the temperature as well as the humidity inside the pipe 41 as well as for regulating the air pressure inside the pipe 41.

Figure 5:
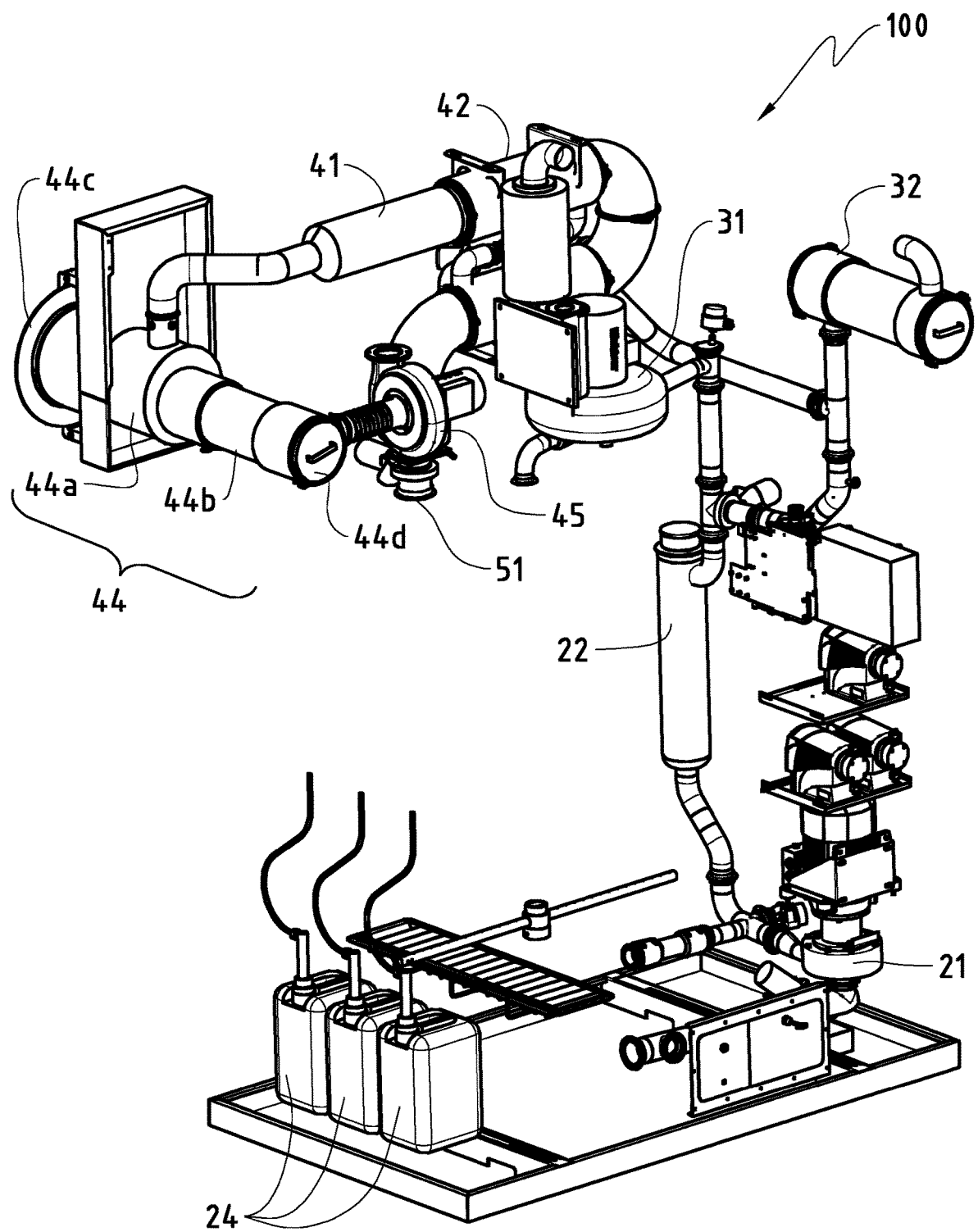
FIG. 5 shows a perspective view of the exhaust filter system according to a preferred embodiment of the present invention.

As can be seen in FIG. 5, the pipe 41 is connected to a so-called push-push filter mechanism 44 containing two HEPA filters. The two HEPA filters are in the so-called primary 44a and secondary 44b positions respectively. The push-push filter mechanism 44 is connected to the blower 45, which ensures circulation of the air exiting the chamber 50 by the air exhaust 51 through the HEPA filters in positions 44a and 44b. The blower 45 allows also for keeping the chamber 50 at a pressure that can be adjusted to 10 Pa to 100 Pa lower than atmospheric pressure all the time the doors 1a and 1b are closed. This ensures that volatile pollutants, such as API, are forced through the filter system 40 and cannot escape the chamber 50 through other means.

The primary HEPA filter in position 44a is designed to be able to filter the air exiting the chamber 50 completely by its own and to ensure that the air existing the blower 45 has an occupational exposure limit value smaller than 1 µm/m3 which corresponds to the band 1 of the in the technical field well-known occupational exposure banding system. The secondary HEPA filter in position 44*b* works as a so-called police filter and ensures that, even if the primary HEPA filter in positon 44*a* is malfunctioning, the air exiting the blower 45 possesses an occupational exposure limit value smaller than 1 μm/m$^3$. Differential pressure sensors are provided to detect malfunction of the HEPA filters. As illustrated in FIG. 5, the push-push mechanism 44 is of the so-called "bag-out" type. This allows for attaching a recycling bag to the exit 44*c* of the push-push mechanism 44 and to push the contaminated primary filter which is in position 44*a* into the recycling bag by means of pushing the secondary filter in position 44*b* into position 44*a* with a new filter that is introduced from the entrance 44*d* of the push-push mechanism 44. Thanks to the bag-out system no pollutants can escape to the environment when exchanging the HEPA filters.

The device 100 further comprises means (not shown here) for introducing an antiseptic gas, advantageously hydrogen peroxide gas, into the chamber 50 to sterilize the polluted components after cleaning. This means advantageously comprises a tank of liquid hydrogen peroxide and a heater for heating hydrogen peroxide above its boiling temperature. Hydrogen peroxide gas introduced in the chamber 50 exits then the latter through the air exhaust 51 and by means of the coolers 42 condensates in the exhaust filter system 40 and is collected by the dripping pan 43. The collected liquid hydrogen peroxide is directed to the drain means 60 of the device 100.

The skilled person will appreciate by reading the description of the preferred embodiment of the present invention, that the device 100 represents a unique combination of a pharmaceutical isolator and a cleaning device. The device can therefore either be seen as an isolator with cleaning ability or a cleaning device with isolator function. The "drive-through" configuration furthermore allows for using device 100 as an "air lock" between a contaminated and a clean space. The ability to introduce antiseptic gas into the chamber 50 allows for the use of the device 100 in a large number of situations in the pharmaceutical industry.

Finally, it should be once again pointed out that the forms of execution described here as examples represent only possibilities for the realization of the inventive ideas and should by no means be regarded as limiting. A person skilled in the art will understand that other implementations of the invention and other elements are possible without neglecting the essential features of the invention.

The invention claimed is:

1. Device for isolating and cleaning contaminated components comprising a chamber, an entrance door through which components to be isolated and cleaned are introducible into the chamber, means configured to deliver washing solution into the chamber and onto the components to be cleaned, a drying system configured to dry the chamber as well as its content, an exhaust filter system attached to an air exhaust of the chamber, the exhaust filter system comprising a pipe, at least one filter, a blower, means for collecting liquid and guiding collected liquid to drain means, and at least one cooler, the exhaust filter system being configured to bring the chamber under a pressure lower than atmospheric pressure by means of the blower all the time the chamber is closed.

2. Device according to claim 1, wherein the exhaust filter system is configured such that air exiting the filter system has an occupational exposure limit smaller than 1 μg/m$^3$.

3. Device according to claim 1, wherein the at least one filter of the exhaust filter system is of type HEPA.

4. Device according claim 1, wherein the exhaust filter system further comprises a primary filter and a secondary filter that are combined into a push-push filter mechanism.

5. Device according to claim 4, wherein the push-push filter mechanism is of type bag-out.

6. Device according to claim 1 wherein the blower is configured to maintain a pressure in the chamber 10 Pa to 100 Pa, advantageously 30 Pa to 70 Pa and even more advantageously 40 Pa to 60 Pa, lower than atmospheric pressure all the time the chamber is closed.

7. Device according to claim 1, further comprising an exit door opposite to entrance door.

8. Device according to claim 7, wherein the exit door further comprises at least two gloves for manipulating objects inside the chamber.

9. Device according to claim 8, further comprising pressurized gas pipes attached to each glove of the exit door.

10. Device according to claim 1, further comprising means by which an antiseptic gas is introducible into the chamber.

11. Device according to claim 10, wherein the antiseptic gas is hydrogen peroxide gas.

12. Device according to claim 1, wherein the entrance door and/or the chamber comprise at least two gloves for manipulating objects inside the chamber, and wherein pressurized gas pipes are attached to each glove of the entrance door and/or the entrance chamber.

13. A method for isolating and cleaning contaminated components by means of a device comprising a chamber, an entrance door through which components to be isolated and cleaned are introducible into the chamber, means configured to deliver washing solution into the chamber and onto the components to be cleaned, a drying system configured to dry the chamber as well as its content, an exhaust filter system attached to an air exhaust of the chamber, the exhaust filter system comprising a pipe, at least one filter, a blower, means for collecting liquid and guiding collected liquid to drain means, and at least one cooler, the exhaust filter system being configured to bring the chamber under a pressure lower than atmospheric pressure by means of the blower all the time the chamber is closed,
wherein the method comprises the steps of:
a. opening the entrance door,
b. introducing the components to be cleaned into the chamber,
c. closing the entrance door,
d. washing the components to be cleaned with washing solution delivered by said means configured to deliver the washing solution into the chamber until the components are clean,
e. drying the cleaned components and the chamber with said drying system,
f. removing the cleaned components from the chamber, wherein,
   all the time the chamber is closed a pressure 10 Pa to 100 Pa lower than atmospheric pressure is maintained inside the chamber by means of the blower of the exhaust filter system of the device.

14. Method according to claim 13, wherein the device further comprises manipulation gloves and wherein the gloves are washed during step (d) and dried during step (e).

15. Method according to claim 13, wherein between steps (d) and (e) the components are rinsed with an aqueous rinsing solution delivered by said means configured to deliver washing solution into the chamber until a predetermined total organic carbon level and/or a predetermined conductivity of the aqueous rinsing solution is reached.

16. Method according to claim 15, wherein the predetermined total organic carbon level of the aqueous rinsing solution is in the range 0.05 ppbc-2 ppmc, advantageously in the range 0.05 ppbc to 1 ppmc, even more advantageously in the range 0.05 ppbc to 0.5 ppmc.

17. Method according to claim 15, wherein the predetermined conductivity of the aqueous rinsing solution is in the range 0.01 µS to 100 µS, more advantageously in the range 0.01 µS to 50 µS, even more advantageously in the range 0.01 µS to 20 µS.

18. Method according to claim 13, wherein between steps (e) and (f) an antiseptic gas is introduced in the chamber.

19. Method according to claim 13, wherein the antiseptic gas is hydrogen peroxide gas.

20. Method according to claim 13, wherein the method is automatically operated by electronic means.

* * * * *